United States Patent
Argersinger et al.

(10) Patent No.: US 6,803,543 B2
(45) Date of Patent: Oct. 12, 2004

(54) HEATED PATIENT DIAGNOSTIC TABLE

(75) Inventors: Andrew Scott Argersinger, Colgate, WI (US); Jonathan Mark Butzine, Oconomowoc, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 246 days.

(21) Appl. No.: 09/683,434

(22) Filed: Dec. 28, 2001

(65) Prior Publication Data

US 2003/0121899 A1 Jul. 3, 2003

(51) Int. Cl.$^7$ ................................................. H05B 3/00
(52) U.S. Cl. ................................... 219/217; 219/211
(58) Field of Search ................................ 219/217, 211, 219/212, 213, 219, 528, 529, 543, 546, 547, 548

(56) References Cited

U.S. PATENT DOCUMENTS

| | | | | |
|---|---|---|---|---|
| 5,324,911 A | * | 6/1994 | Cranston et al. | 219/218 |
| 5,643,480 A | * | 7/1997 | Gustavsson et al. | 219/211 |
| 6,194,692 B1 | * | 2/2001 | Oberle | 219/543 |

* cited by examiner

*Primary Examiner*—Edward K. Look
*Assistant Examiner*—Vinod D. Patel

(57) ABSTRACT

A heated patient diagnostic table 10 is provided, including a tabletop 12 and a heater array 14 in communication with the tabletop 12. The heater array 14 includes a conductive polymer coating 16 compatible for use in medical diagnostic imaging systems. The conductive polymer coating 16 is utilized to produce thermal energy capable of heating the tabletop 12 and thereby increase patient comfort.

21 Claims, 2 Drawing Sheets

HEATED PATIENT DIAGNOSTIC TABLE

BACKGROUND OF INVENTION

The present invention relates generally to a medical diagnostic table and more particularly to a heated medical diagnostic table for increased patient comfort.

Modern medical facilities often subject patients to a cold, austere, and sterile environment. While certain aspects of these environments are necessitated by the desire to safeguard a patient's health, others merely serve to increase the discomfort the patients may already be experiencing. The thin gowns worn by patients, while allowing quick and easy access to the patient's body for diagnosis or treatment, often result in exposed skin or lightly covered skin that is vulnerable to the cold surfaces of the medical environment. This exposure can result in discomfort and may undesirably stress the patient. While this is undesirable for any patient, additional concerns may be raised when seriously ill or injured patients are exposed to these added stressors.

In addition to causing general discomfort, cold surfaces within the medical environment may provide additional complications. During examination where patients may need to hold particular positions, cold medical surfaces can act as heat sinks to the human skin and pull heat from the body. This may make it difficult for the patient to remain in the particular position necessary for examination. When the patient must be on the exam table for long periods of time, this increased patient discomfort may further increase exam time by inducing patient motion and thereby requiring repositioning of the patient. In addition, patient movement during imaging can result in undesirable double exposure images. It would therefore, be highly desirable to increase the comfort of such surfaces such that patient comfort discomfort is decreased and examination procedures can be simplified.

Although the application of heat to a diagnostic table may on its surface appear to be a straightforward proposition, design constraints associated with medical imaging can present complications for the use of many heating methodologies. Electrical coils, for example, may result in electrical interference with some imaging technologies. Other technologies may absorb x-rays or other imaging signals and thereby prove impractical. Additionally, even inert heating methodologies such as fluid flow may prove impractical by requiring noisy and bulky pumping systems. Furthermore, the ability to retrofit existing diagnostic tables may be hampered by the use of complex bulky designs. Non-interference, small profile, low cost, and the ability to retrofit can be important design considerations for a heated medical diagnostic table.

It would, therefore, be highly desirable, to have a heated medical diagnostic table having a heating element with a relatively small profile, that did not interfere with medical imaging signals, and that could be easily retrofitted to existing medical diagnostic tables.

SUMMARY OF INVENTION

It is, therefore, an object of the present invention to provide a cost effective, non-interfering, low profile heat generating medical diagnostic table with positive retrofitting characteristics.

In accordance with the objects of the present invention, a heat generating medical diagnostic table is provided. The heat generating medical diagnostic table includes a heater array comprising a conductive polymer coating bonded to a film base.

Other objects and features of the present invention will become apparent when viewed in light of the detailed description of the preferred embodiment when taken in conjunction with the attached drawings and appended claims.

DETAILED DESCRIPTION

Figure 1:
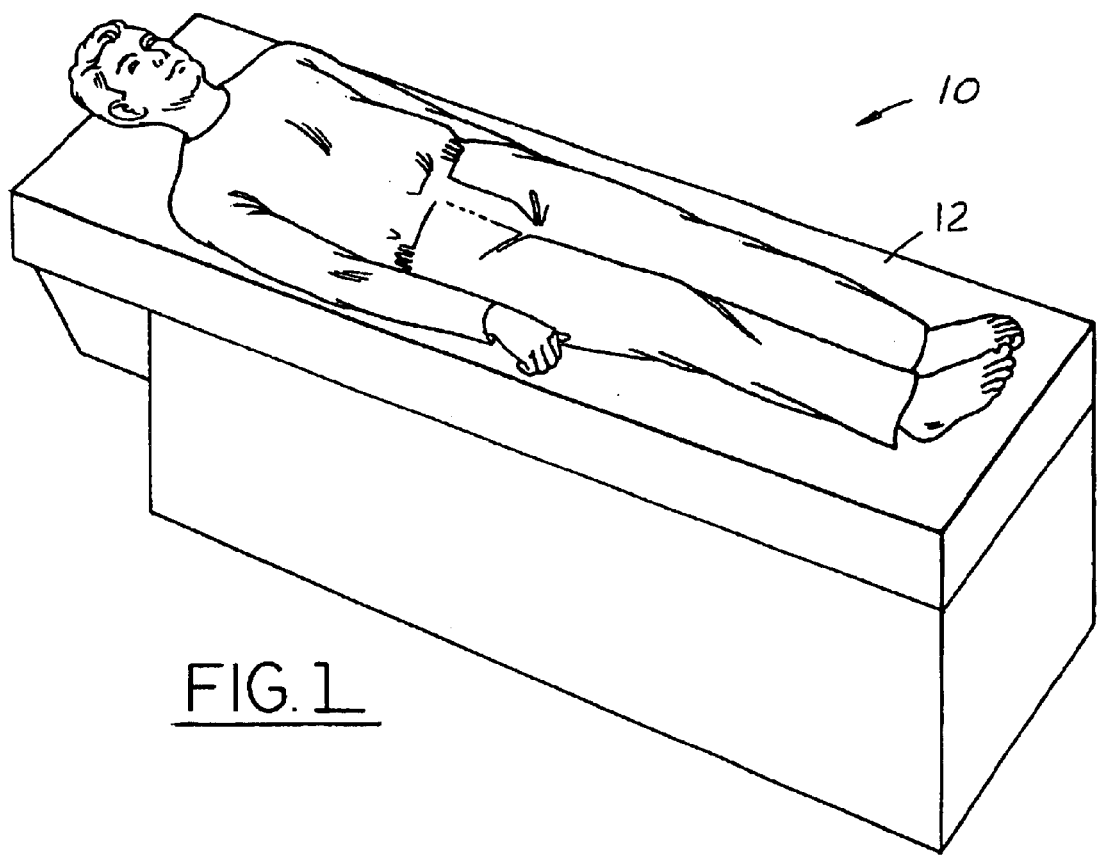
FIG. 1 is an illustration of an embodiment of a heated patient diagnostic table in accordance with the present invention.
Figure 2:
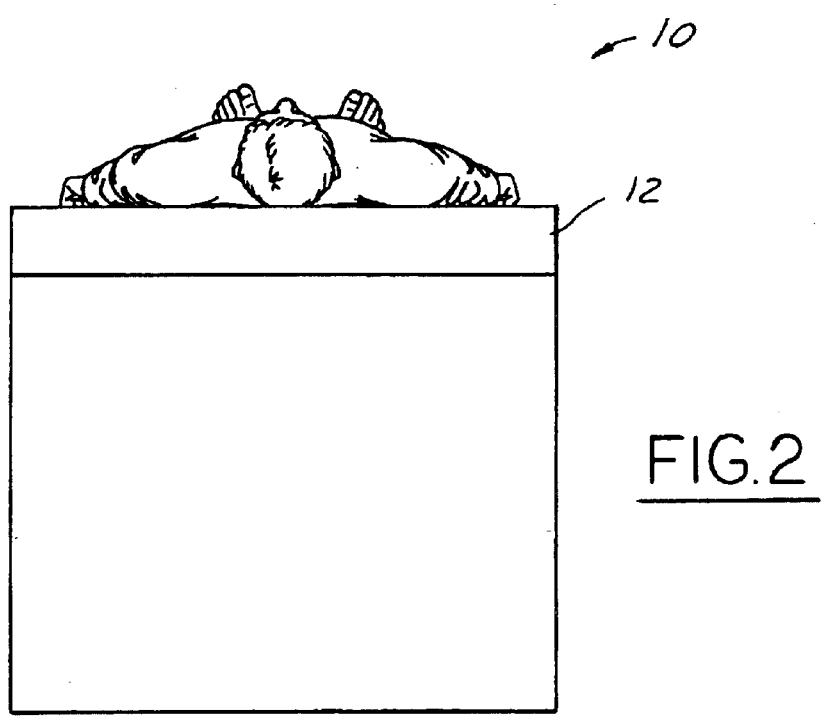
FIG. 2 is an illustration of an embodiment of a heated patient diagnostic table in accordance with the present invention.

Referring now to FIGS. 1 and 2, which are illustrations of a heated patient diagnostic table 10 in accordance with the present invention. It is well known that patient diagnostic tables 10 come in a variety of shapes and forms. Some examples may be geared towards personal examination of patients, while others may be configured for interaction with complex diagnostic imaging equipment. The configuration illustrated in FIGS. 1 and 2 is simply for illustrative purposes and is not intended to serve as a limitation on the present invention. Furthermore, the term "table" is intended to encompass any diagnostic surface including a wide variety of sizes and configurations. Tables may be horizontal, vertical, or at a variety of angles. Similarly, they may be sized in relation to an entire human body, or merely a portion. The term "table" is not intended to limit the present invention to a horizontal, full body surface.

Figure 3:
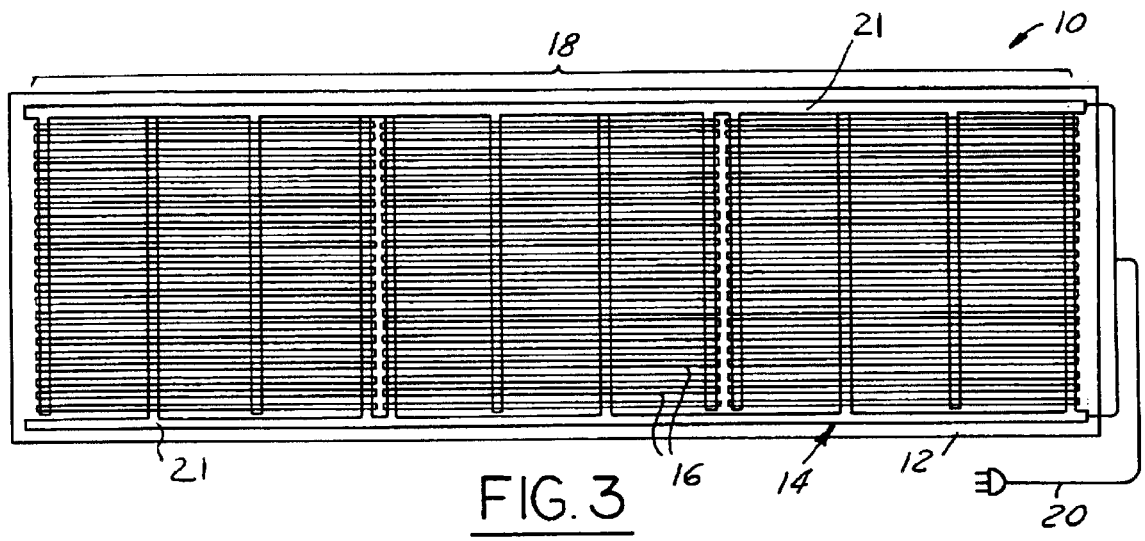
FIG. 3 is a bottom-view illustration of a heated patient diagnostic table in accordance with the present invention.

Referring now to FIG. 3, which is a bottom-view illustration of a heated patient diagnostic table 10 in accordance with the present invention. A heated patient diagnostic table 10 includes a table surface 12 and a heater array 14. The heater array 14 is composed of a conductive polymer coating 16. Although the heater array 14 represents a novel approach to creating a heated patient diagnostic table 10, the use of conductive polymer coatings 16 to create a heater array 14 is well known in non-analogous arts such as automotive heated seat designs, heat skin boots, de-icing antennas, chemical tank heaters, anti-fogging technology, cup warmers, and even stadium cushions. The use of the conductive polymer coating 16 in order to heat the heated patient diagnostic table 10 is highly beneficial in that the technology is well-suited for close contact to skin and can be utilized with the safe voltage and current limits. Even more significantly, the conductive polymer coating 16 does not produce significant image artifacts or absorb a significant amount of x-rays, and therefore make them well-suited for the low interference characteristics required by medical diagnostic imaging.

A wide variety of conductive polymer coatings 16 are known and contemplated by the present invention. In one embodiment, however, the conductive polymer coating 16 includes carbon flakes suspended in a liquid polymer. The flakes can be produced in a certain density such that they overlap by ⅔ and are in layers to create carbon coverage within a printed area. The resistance properties can be varied by varying the concentration of the carbon flake/polymer blend. The conductive polymer coating 16 can then be printed onto a surface and fired. The firing applies heat as is well understood within the art, and can burn off solvents from the liquid polymer and bond the conductive polymer coating 16 to the surface on which it is placed. The printing pattern, as well as the properties of the conductive polymer coating 16 can be utilized to produce a wide variety of heater arrays 14 that are formed in a wide variety of configurations. In addition, although a single form of the conductive polymer coating 16 has been described, a variety of forms and methods of producing a conductive polymer coating 16 are contemplated by the present invention.

Although the conductive polymer coating 16 may be formed in a variety of configurations, in one embodiment it is formed as a grid pattern 18. In another embodiment, the conductive polymer coating can be formed in a continuous pattern. The configuration of the conductive polymer coating 16 can be varied to create anywhere between a sparse and a completely populated heater array 14 and thereby provides flexibility and adaptability for individual designs. As electricity passes through the grid pattern 18 from the power cord 20, the electricity encounters resistance from a conductive polymer coating 16. This, in turn, produces heat. Current may be adjusted or controlled using a variety of techniques and controls well known in the art such that a variety of heating profiles and temperatures may be created and the table surface 12 temperature may be controlled for a given application. In addition, power may be supplied to the conductive polymer coating 16 in a variety of fashions. In one embodiment, a power cord 20 can be connected to supply power to the conductive polymer coating 16. Additionally, at least one runner 21 can be utilized to transfer current to from the power cord 20, or other power supply, to the conductive polymer coating 16. The use of runners 21 is well known in the art. Runners 21 are preferably thin flat conductive laminates that carry current along the edges of the heater array 14 such that the entire heater array 14 is supplied with power. Although the present invention can be utilized with or without runners 21 and with runners 21 in a variety of positions, one embodiment contemplates the positioning of the runners 21 along the side of the heater array 14. By placing runners 21 along the sides of the heater array 14 it may make it easier to hide the runners 21 from the visible area of the table top 12. This allows the runners 21 to be placed outside the visible area of an x-ray image to minimize interference.

Figure 4:
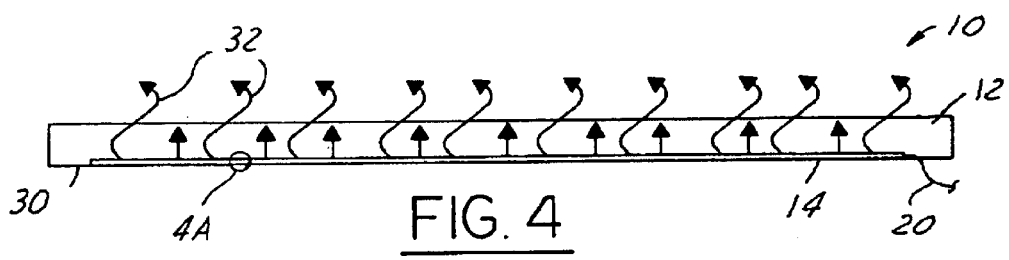
FIG. 4 is a side-view illustration of the heated patient diagnostic table shown in FIG. 3.
Figure 4A:
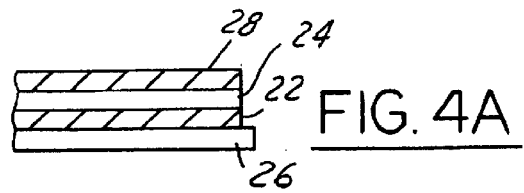
FIG. 4A is a detail illustration of a portion of the heated patient diagnostic table illustrated in FIG. 4, the detail taken from the portion marked 4A.

Referring now to FIG. 4, which is a side-view illustration of the heater array 14 illustrated in FIG. 3. Although in its most simplistic form, the heater array 14 can consist solely of a conductive polymer coating 16, additional components may be utilized to improve the heated patient diagnostic table 10. The conductive polymer coating 16 can be formed onto a film base 22 such as a polyester film. This creates a flexible and transportable heater array 14 suitable for retrofitting existing diagnostic tables. The conductive polymer coating 16 can also be covered with an additional protective film layer 24 for protection. Although, the additional protective film layer 24 may be formed using a variety of materials, in one embodiment the protective film layer 24 is formed using polyester as well. The additional protective film layer 24 can be utilized to prevent damage to the heater array 14 as well as allow the heater array 14 to be mounted to a variety of surfaces without concern for creating electrical shorts.

A reflective element 26 may additionally be included in order to direct the radiant heat produced by the heater array 14 in a direction suitable for usage. Although many configurations are contemplated, in one embodiment the reflective element 26 is utilized to direct heat generated by the heater array 14 up through the table surface 12. It should be understood that the reflective element 26 is an optional element. As the heated patient diagnostic table 10 may be powered by a variety of sources including both d/c and a/c sources, the reflective element 26 may be utilized additionally as a ground. Although the reflective element 26 may be formed using a variety of known materials, it is desirable to form the reflective element to minimize its effect on the attenuation of the imaging signal. In some circumstances, it may be preferable not to use a reflective element 26 where its effect on signal attenuation is undesirable.

A wide variety of optional additional components, such as thermostats, gauges, control modules, and displays may be used in conjunction with the conductive polymer coating 16 in order to further increase the effectiveness of the heat array 14. An adhesive element 28, for example, may also be included to create a convenient mounting methodology to attach the heater array 14 to the tabletop 12. Although the individual components may be arranged in a variety of fashions, in one embodiment is contemplated that the adhesive 28, the reflector element 26, protective film layer 24, and the film base 22 may be laminated together to create highly effective heating unit suitable for retrofitting onto existing diagnostic tables.

Figure 5:
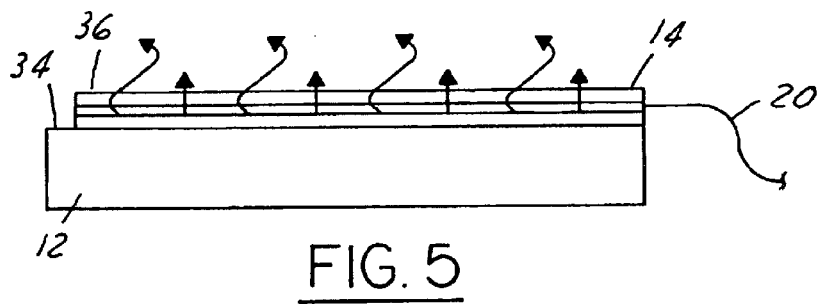
FIG. 5 is a side-view illustration of an alternate embodiment of a heated diagnostic table in accordance with the present invention.

It is contemplated that the heat array 14 may be mounted or secured to the tabletop 12 in a variety of fashions. The optional adhesive 12, as described, allows a convenient method of attachment that may also allow the heat array 14 to be conveniently retrofitted onto existing tabletops 12. In one embodiment, illustrated in FIG. 4, the heater array 14 is affixed to the bottom surface 30 to the tabletop 12. In this scenario, thermal energy 32 is radiated up through the tabletop 12 such that the table surface 32 can be maintained at a temperature appropriate for skin contact. In an alternate embodiment, illustrated in FIG. 5, the heater array 14 may be positioned within a tabletop accessory pad 36 that may be positioned on the upper surface 34 of the tabletop 12. This allows the heater array 14 to be used in even difficult retrofitting situations where access to the bottom surface 32 of the tabletop 12 may not be feasible.

While particular embodiments of the invention have been shown and described, numerous variations and alternative embodiments will occur to those skilled in the arm. Accordingly, it is intended that the invention be limited only in terms of the appended claims.

What is claimed is:

1. A heated patient diagnostic table comprising:
   a tabletop element; and
   a heater array comprising a conductive polymer coating bonded to a film base, said heater array in communication with said tabletop element;
   wherein said conductive polymer coating comprises carbon flakes suspended in a liquid polymer.

2. A heated patient diagnostic table as described in claim 1 further comprising:
   a protective film layer element laminated to said film base.

3. A heated patient diagnostic table as described in claim 1 further comprising:
   at least one reflective element laminated to said film base.

4. A heated patient diagnostic table as described in claim 1 wherein said conductive polymer coating is formed in a grid pattern.

5. A heated patient diagnostic table as described in claim 1 further comprising:
   at least one runner, said at least one runner in electrical communication with said heater array.

6. A heated patient diagnostic table as described in claim 1 further comprising:
   a tabletop element having an upper surface and a lower surface;
   wherein said heater array is mounted to said lower surface of said tabletop.

7. A heated patient diagnostic table as described in claim 6 wherein said heater array is mounted to said lower surface through the use of an adhesive element.

8. A heated patient diagnostic table comprising:
   a tabletop having an upper surface and a lower surface; and
   a heater array controlling the temperature of said tabletop element, said heater array in thermal communication with said tabletop element and comprising a conductive polymer coating bonded to a film base and a protective film layer laminated to said film base.

9. A heated patient diagnostic table as described in claim 8 wherein said conductive polymer coating comprises carbon flakes suspended in a liquid polymer.

10. A heated patient diagnostic table as described in claim 8 wherein said heater array is mounted to said tabletop using an adhesive.

11. A heated patient diagnostic table as described in claim 8 wherein said heater array further comprises:
    a reflector element mounted to said film base.

12. A heated patient diagnostic table as described in claim 8 wherein said heater array is mounted to said bottom surface of said tabletop element.

13. A heated patient diagnostic table as described in claim 8 wherein said film base comprises polyester.

14. A heated patient diagnostic table as described in claim 8 wherein said conductive polymer coating is formed in a grid pattern.

15. A patient diagnostic pad assembly comprising:
    a tabletop element;
    a diagnostic table accessory pad in communication with said tabletop element; and
    a heater array positioned within said tabletop accessory pad and comprising a conductive polymer coating bonded to a film base.

16. A patient diagnostic pad assembly as recited in claim 15 wherein said conductive polymer coating comprises carbon flakes suspended in a liquid polymer.

17. A patient diagnostic pad assembly as recited in claim 15 further comprising:
    a protective film layer mounted to said film base.

18. A patient diagnostic pad assembly as recited in claim 15 further comprising a reflective element mounted to said film base.

19. A patient diagnostic pad assembly as recited in claim 15 further comprising:
    at least one runner.

20. A patient diagnostic pad assembly as described in claim 19 wherein said at least one runner is positioned on the side of said heater array.

21. A patient diagnostic pad assembly as described in claim 15, wherein said base comprises polyester.

* * * * *